United States Patent
Diallo et al.

(10) Patent No.: US 7,038,922 B2
(45) Date of Patent: May 2, 2006

(54) DIRECT ENERGY TRANSFER CONVERTER

(75) Inventors: Almadidi Diallo, Thorigne-Fouillard (FR); Philippe Puisieux, Lannion (FR); Jean-Marie Thereze, Lannion (FR)

(73) Assignee: Alcatel, Paris (FR)

( * ) Notice: Subject to any disclaimer, the term of this patent is extended or adjusted under 35 U.S.C. 154(b) by 43 days.

(21) Appl. No.: 10/778,197

(22) Filed: Feb. 17, 2004

(65) Prior Publication Data

US 2004/0160790 A1    Aug. 19, 2004

(30) Foreign Application Priority Data

Feb. 18, 2003    (FR)    .................... 03 01914

(51) Int. Cl.
*H02M 3/335*    (2006.01)
(52) U.S. Cl. ........................ 363/21.6; 363/127; 363/20
(58) Field of Classification Search .................. 363/16, 363/17, 19, 81–90, 127, 20, 21.4, 97, 95, 363/21.6
See application file for complete search history.

(56) References Cited

U.S. PATENT DOCUMENTS 5,430,640 A    7/1995    Lee
5,818,704 A *  10/1998   Martinez .................. 363/21.06
6,061,255 A    5/2000    Chik et al.
6,185,114 B1   2/2001    Matsumoto et al.

* cited by examiner

*Primary Examiner*—Rajnikant B. Patel
(74) *Attorney, Agent, or Firm*—Sughrue Mion, PLLC

(57) ABSTRACT

The invention concerns a direct energy-transfer converter of the AC/AC or DC/DC type, including a self-regulated synchronous rectifier, in which the rectifier switches are controlled through one or more transformer windings. The converter includes a primary stage with at least one primary winding of a transformer and at least one controlled switch, with a secondary stage having at least one secondary winding (10) of the transformer, and a synchronous rectifier (1) with at least a first switch (20) which is self-regulated and conducting during the conducting phase of the controlled switch of the primary stage, known as the direct energy-transfer stage, and at least one secondary switch (30) which is self-regulated and conducting during the non-conducting phase of the controlled switch of the primary stage, known as the freewheel phase, and an output filter (5). Said converter also includes the means (CTC1) to render conducting said second switch (30) independently of the voltage at the terminals of the secondary winding (10) during said freewheel phase.

12 Claims, 5 Drawing Sheets

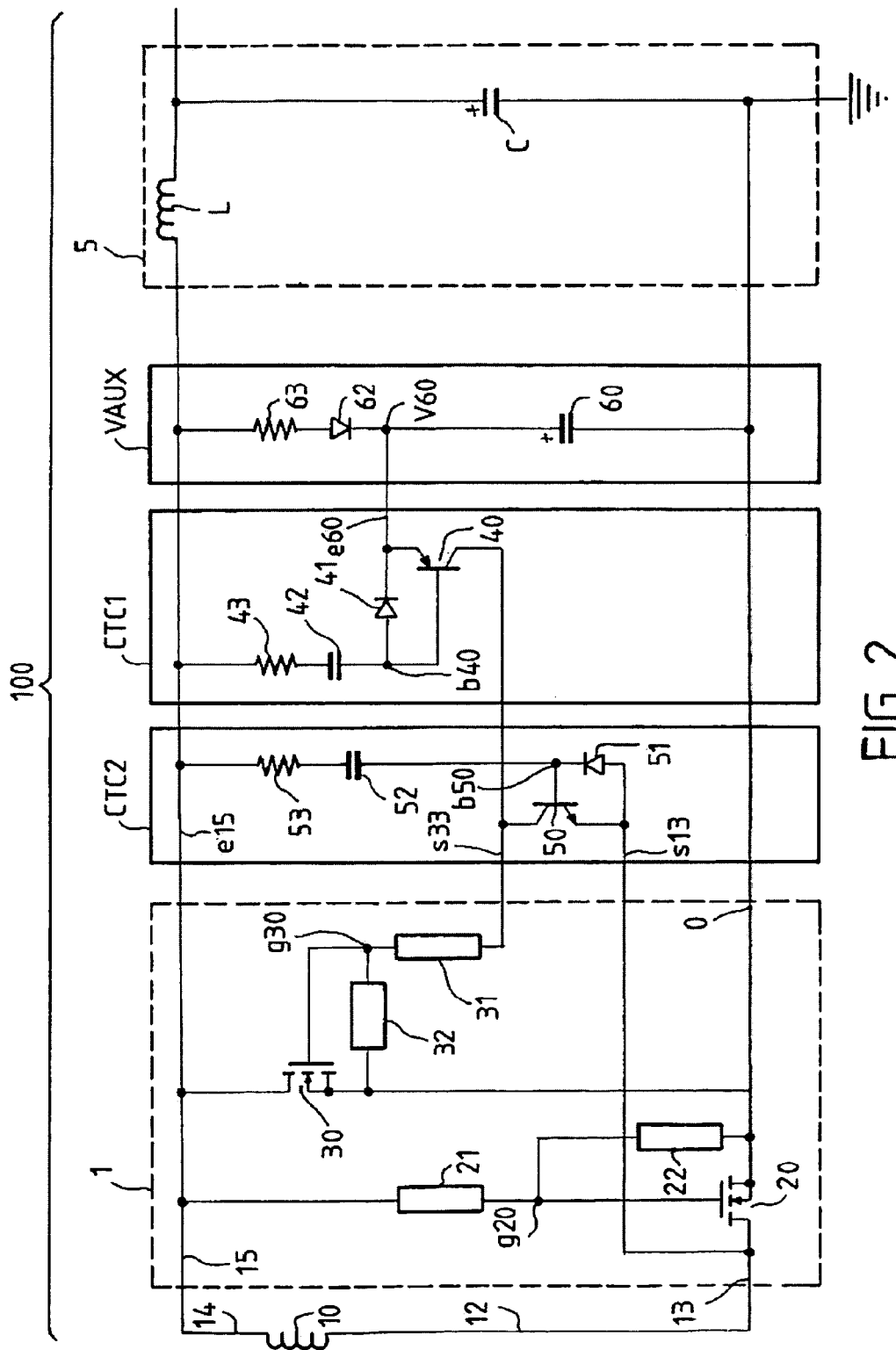
FIG_2

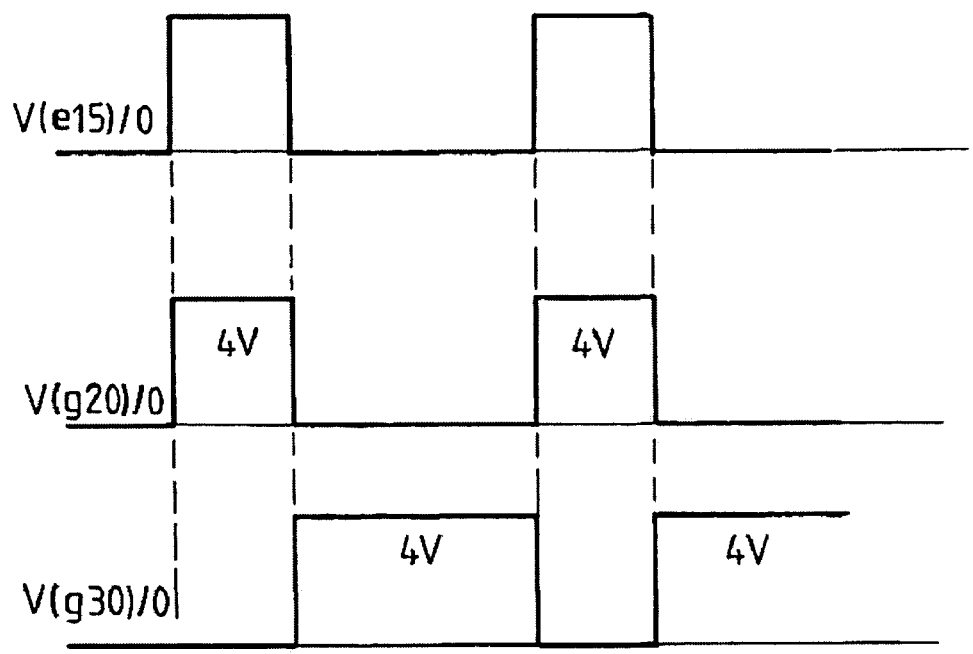
FIG_3

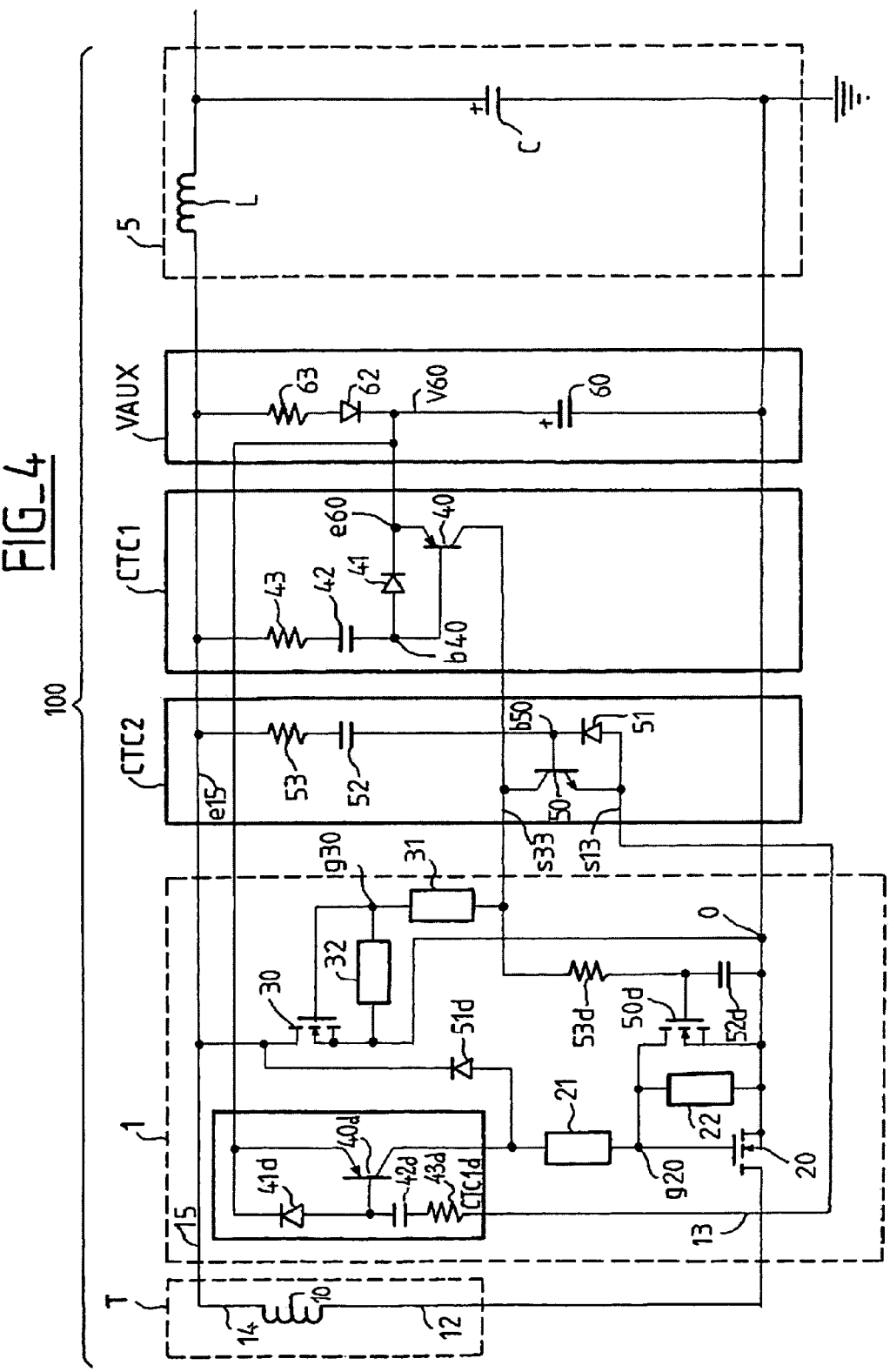

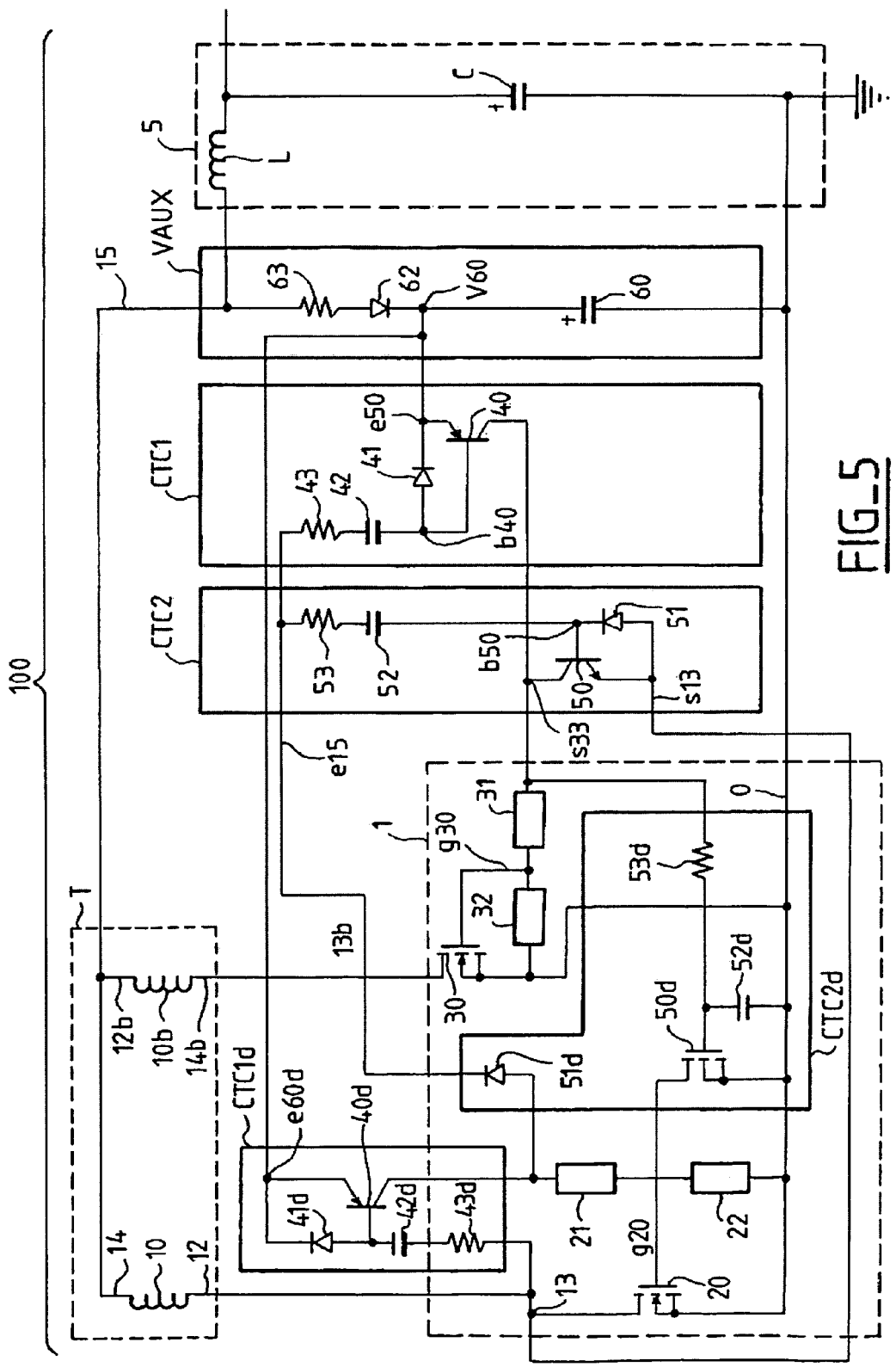
FIG_5

DIRECT ENERGY TRANSFER CONVERTER

BACKGROUND OF THE INVENTION

The invention concerns a direct energy-transfer converter of the AC/AC or DC/DC type, consisting of a self-regulated synchronous rectifier. In the remainder of this document, the expression "synchronous rectifier" preferentially refers to a self-regulated synchronous rectifier, meaning a rectifier in which the rectifying switches are controlled over one or more transformer windings.

Direct energy transfer conversion systems are known which include an input voltage source and at least one controlled primary switch, driving a transformer whose secondary is fitted with at least two power switches constituting a self-regulated synchronous rectifier. Said synchronous rectifier is mounted in cascade with a filter delivering a continuous controlled voltage into an application. In this type of conversion chain, the purpose of the rectifier is:

- to deliver to the application, through the filter, the energy transferred by the transformer during the conducting period of the primary switch, called the direct transfer phase, and
- to block the transfer during the non-conducting period of said primary switch, the application being supplied by the coil of the filter through a freewheel switch, such as a MOSFET, from the rectifier, during this non-conducting period of the main primary switch, called the freewheel phase.

The secondary part (100) of such a converter of the asymmetrical direct energy transfer type, is represented on FIG. 1. Rectification is said to be of the "active clamp" type.

Part 100 includes:
a secondary winding (10) of the power transformer,
a synchronous rectifier (1) of the direct transfer type,
an LC output filter (5).

The synchronous rectifier (1) includes two secondary power transistors (20 and 30) and their respective control elements (21–22 and 31–32), arranged so as to ensure direct transfer of energy via the transistor (20) and the freewheel phase implemented by transistor 30, with the minimum of losses. Elements 21 and 31 are a diode in parallel with a capacitance, for example, and elements 22 and 32 are Zener diodes, for example.

This solution is possible only by optimisation of the gate control voltages. The wiring of the self-regulated control elements results in voltages on the gates of the power transistors whose amplitudes are directly dependent on the input voltage to the terminals of the primary winding (not shown) and therefore the output voltage at the terminals of the secondary winding (10). In asymmetrical direct energy transfer systems of the active clamp type, the amplitudes of the gate voltages vary in the opposite sense. For example, the voltage available at the gate of transistor 20, in the direct phase, is maximum for a maximum input voltage. Conversely, when the input voltage reduces, the voltage available at the gate of transistor 30 increases, to reach a maximum value that may be unsuitable.

The result is that this solution gives rise to a certain number of difficulties. It can happen, in fact, that the maximum gate voltage of one of the two transistors is not sufficient to effect control. This is the case in particular when the voltage at the terminals of the secondary winding (10) is low, at about 2V. A low voltage at the terminals of the secondary winding can, in particular, occur in the case of a variable input voltage at the terminals of the primary winding, of 36V and 72V, for example, for an average voltage of 48V, or between 18V and 36V for an average voltage of 24V, and even more so for wider variations of input voltage, such as 18V–72V. The voltage at the terminals of the secondary winding can then be just sufficient to control transistor 20 in the direct phase, but insufficient to control transistor 30 in the freewheel phase.

Conversely, for high output voltages, above 10V, it is not easy to find a good compromise between an adequate gate voltage on the direct transistor, over the whole input voltage range, and maximum gate voltage but less than the maximum value allowable for the gate of the freewheel transistor.

SUMMARY OF THE INVENTION

This present invention aims at creating a direct energy transfer converter by self-regulated synchronous rectifier, of the active clamp type in particular, enabling the removal of both the conduction losses, due to inadequacy of the control voltages when the output voltage is low, and the switching losses generated when the output voltage is high, by guaranteeing an sufficient control voltage in both the freewheel and direct phases.

To this end, this present invention proposes a direct energy transfer converter which includes:
- a primary stage with at least one primary winding of a transformer and at least one controlled switch with conducting and non-conducting operating phases.
- a secondary stage with at least one secondary winding of said transformer and a synchronous rectifier, which includes:
  - at least a first switch, called the direct switch, which is self-regulated, and conducting during said conducting stage of said controlled switch of the primary stage, called the direct energy transfer phase,
  - at least a second switch, called the freewheel switch, which is self-regulated and conducting during the non-conducting phase of said controlled switch of the primary stage, known as the freewheel phase,
  - an output filter,
- where said converter has first self-regulated means, triggered in accordance with the voltage at the terminals of said secondary winding, and applying, to the secondary switch, a corresponding control voltage suitable to render conducting said secondary switch, characterised in that said first self-regulated means include a first charge-transfer circuit, controlled directly by said voltage at the terminals of said secondary winding, to apply to the second switch a control voltage which is more or less constant and supplied by an auxiliary voltage source.

By virtue of the invention, control of the second switch in order to pass into the freewheel stage is independent of the voltage at the terminals of the secondary winding during the freewheel phase. Thus a variation of the input voltage which, in the freewheel phase, would lead to a drop in the voltage at the terminals of the secondary winding, has no effect on the control of the secondary freewheel switch.

With advantage, the auxiliary voltage source will take the form of the simplest possible circuit, but provided that it is able to supply a suitable voltage in every case, depending on the context of converter use.

Thus, for reasons of compactness and cost, is will be generally preferable that the auxiliary voltage source should obtain its energy from the converter itself. This can be obtained at the output of the converter, that is downstream of the filter.

However a particularly useful solution, in the event that the converter output voltage is liable to fall too low, is that the auxiliary voltage source could supply a voltage which is more or less equal to the voltage of the secondary winding during the direct phase. Thus the auxiliary voltage source is a circuit which is designed to store the energy supplied by the secondary winding, at a voltage which is more or less equal to the peak voltage available at its terminals. This arrangement enables producing a voltage which is larger than that which can be obtained at the output of the converter, since the latter is only the mean voltage present at the terminals of the secondary winding.

According to a first alternative of the invention, the control voltage of said first switch is obtained from the voltage at the terminals of said secondary winding.

Thus the voltage of the secondary winding is chosen to optimise the control of the first direct energy transfer transistor switch. The control voltage of the second switch enabling entry into the freewheel phase is directly related to the control voltage enabling entry into the direct energy transfer phase. The converter, according to the invention, thus enables optimisation of control of the first switch without having concern itself about control of the second switch.

According to a second alternative of the invention, said converter includes second self-regulated means to apply a control voltage which renders said first switch conducting in the direct phase, where this control voltage is supplied by said auxiliary voltage source by means of a second charge transfer circuit.

Thus this second alternative is used to control both switches of the converter, using a predetermined control voltage, for example, from a voltage which is more or less equal to the voltage of the secondary winding during the direct phase.

Said first and second switches are advantageously MOSFET transistors.

According to a particular embodiment of the invention, said auxiliary voltage source includes:
  a capacitance,
  a rectifier element connected at one end is series with said secondary winding, where said rectifier creates an auxiliary voltage which is more or less equal to the voltage of the secondary winding during the direct phase.

According a particular embodiment of the invention, said first and second switches are MOSFET transistors, and said first charge transfer circuit includes:
  a bypass network consisting of a capacitance connected in series with a resistance, said resistance is connected to one end of said secondary winding, and where said network detects the variation of voltage induced by said primary winding at the terminals of said secondary winding.
  a bipolar transistor, called the charge transistor, where the base of said bipolar transistor is controlled via said network, and the emitter of said transistor is connected to said auxiliary voltage source, and the collector of said bipolar transistor is connected to the gate of said second switch.

Advantageously, according to this particular embodiment of the invention, a diode is mounted in anti-parallel between the base and emitter of said bipolar charge transistor.

In a particularly advantageous manner, the converter includes means for anticipating the cut-off of said second switch before said first switch begins to conduct in said direct phase.

According a particular embodiment of the invention, said first and second switches are MOSFET transistors, and said means to anticipate cut-off of said second switch before the first switch begins to conduct in said direct phase includes:
  a bypass network consisting of a capacitance connected in series with a resistance, where said resistance is connected to one end of said secondary winding, and where said network detects the variation of voltage induced by said primary winding at the terminals of said secondary winding.
  a bipolar transistor, called anticipation transistor, where the base of said bipolar transistor is controlled via said bypass network, where the emitter of said transistor is connected to the drain of said first switch, and the collector of said bipolar transistor is connected to the gate of said second switch.

Advantageously, according to this last embodiment of the invention, a diode is mounted in anti-parallel between the base and emitter of said bipolar anticipation transistor.

Advantageously, said first and second switches are MOSFET transistors, and said second charge transfer circuit includes:
  a bypass network consisting of a capacitance connected in series with a resistance, where said resistance is connected to one end of said secondary winding, and where said network detects the variation of voltage induced by said primary winding at the terminals of said secondary winding.
  a bipolar transistor, called charge transistor, where the base of said bipolar transistor is controlled via said network, and the emitter of said transistor is connected to said auxiliary voltage source, and the collector of said bipolar transistor is connected to the gate of said first switch.

Advantageously, said converter includes means to delay switching on of said first switch while said second switch is being controlled.

Advantageously, said first and second switches are MOSFET transistors, and said means for delaying switch-on of said first switch while said second switch is being controlled includes:
  a MOSFET transistor, called delay transistor,
  a resistance with a first terminal connected to the gate of said freewheel transistor, and a second terminal connected to the gate of said delay transistor,
  a capacitance with one terminal connected to the gate of said delay transistor and a second terminal connected to the source of said direct transistor.

In an advantageous manner, said primary stage and said secondary stage are isolated galvanically.

Thus, the circuit retains a galvanic isolation which is frequently essential in this type of converter for reasons of safety.

BRIEF DESCRIPTION OF THE DRAWINGS

Other characteristics and advantages of this present invention will appear in the following description in accordance with the methods of implementation of the invention, provided for illustrative purposes only, and without limitation.

In the following figures:
FIG. 3 shows voltage diagrams as a function of time, relating to a converter with a secondary part as represented on FIG. 2, FIG. 4 schematically shows the secondary part of a direct energy transfer converter according to a second embodiment of the invention, FIG. 5 schematically shows the secondary part of a direct energy transfer converter according to a third embodiment of the invention.

DETAILED DESCRIPTION OF THE INVENTION

Figure 1:
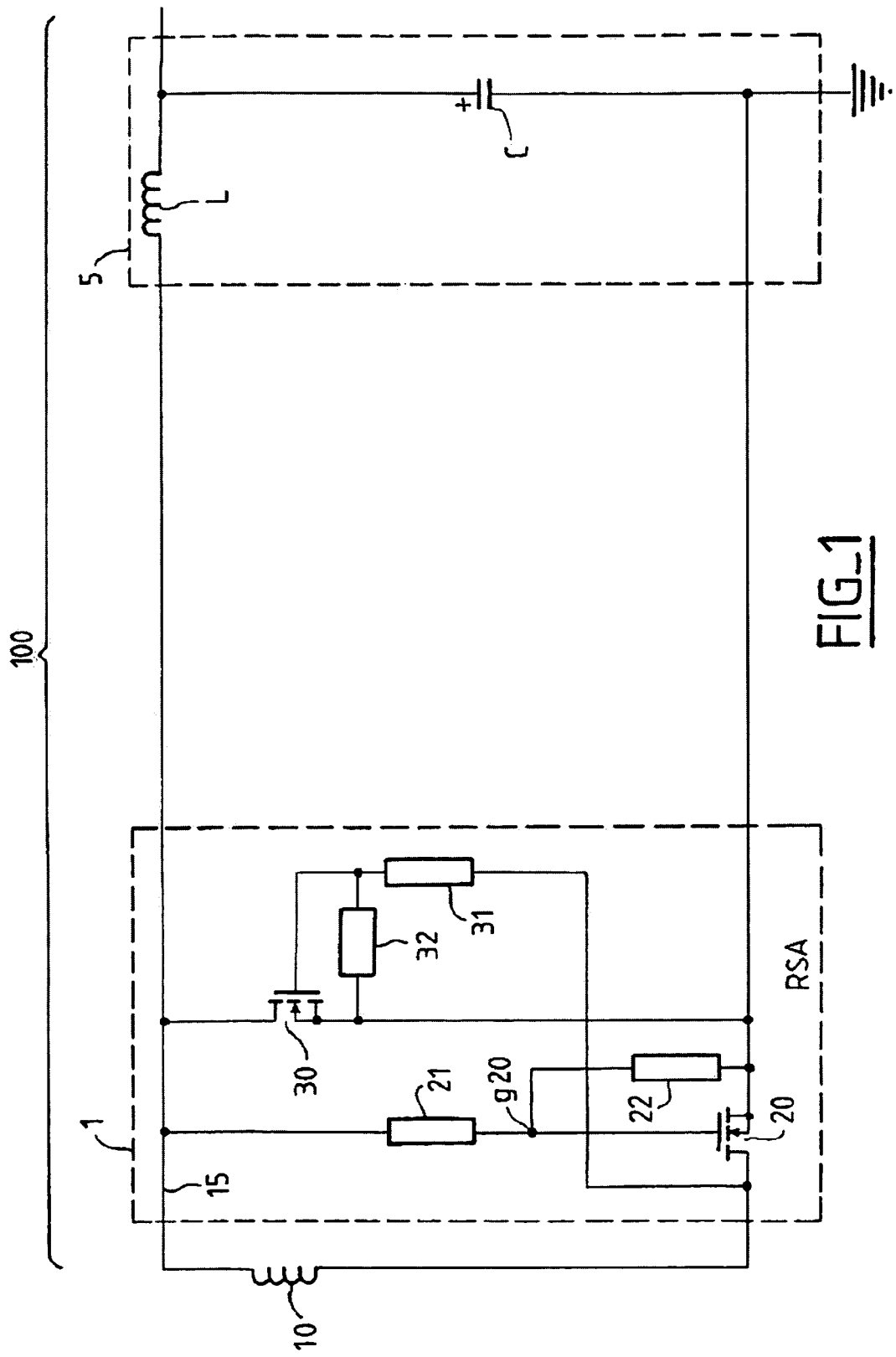
FIG. 1 schematically shows the secondary part of a direct energy transfer converter according to background art,
  FIG. 2 schematically shows the secondary part of a direct energy transfer converter according to a first embodiment of the invention.

On all of the figures, the common elements bear the same reference numbers. FIG. 1 has already been described in relation to the state of the art.

FIG. 2 represents the secondary part (100) of a direct energy transfer converter (100) according to a first embodiment of the invention. Note that the primary part of the converter, which is not represented here, is implemented in a known manner, using a primary winding of a power transformer wired to an input voltage source, by means of switching elements mounted preferentially in direct energy transfer with active clamping.

Part 100 includes:
a secondary winding (10) of a power transformer,
a synchronous rectifier (1) of the direct energy transfer type,
an LC output filter (5),
means CTC1, called the first charge-transfer circuit,
means CTC2, called the second charge-transfer circuit,
an auxiliary voltage source (VAUX).

The synchronous rectifier (1) includes two secondary switches in the form of two MOSFET power transistors (20), (direct MOSFET) and (30) (freewheel MOSFET), which respectively implement the direct and freewheel phases of rectifier 1.

The gate of the power transistor (20) guaranteeing the direct energy transfer is controlled by the secondary power winding (10) via impedances 21 and 22, where impedance 21 is connected between the gate of transistor 20 and the end (15) of winding (10) and impedance 22 is connected to the gate and the source of transistor 20.

Means CTC1 and CTC2 are control means of the freewheel MOSFET transistor, and will be described in greater detail hereafter:

The secondary power winding (10) includes:
a first end (14) connected to the common input (15) of the rectifier (1), the output filter, and the input (e15) of the charge-transfer circuits CTC1 and CTC2.
a second end (12) connected in series with the input (13) of the rectifier (1).

Inputs 15 and 13 of said rectifier (1) are connected respectively to the MOSFET transistor (30 and 20) effecting the freewheel and direct energy transfer phases.

The voltages of the secondary stage are referenced in relation to the sources of the power switches (20 and 30) connected to point 0 of the rectifier (1). Point 0 therefore acts as a ground for the secondary part (100).

The auxiliary voltage source (VAUX), available at point V60, has a resistance (63), a diode (62) and a charge capacitance (60) connected in series, this series circuit being connected between the end (14) of the winding (10) and the ground at point 0.

Means CTC1 include a transistor (40), known as the charge transistor, which is a signal pnp bipolar transistor type. Note that transistor 40 can be a P-channel signal MOSFET transistor, but only the creation of means CTC1 using a pnp type bipolar transistor will be described.

The collector of the pnp bipolar signal transistor (40) is connected to the gate (g30) of the freewheel transistor (30) via an optional impedance (31), impedance 31 being equated to a short circuit in the remainder of the document.

The base of the bipolar transistor (40) is controlled via an RC by-pass network composed of a capacitor (42) in series with a resistance (43) connected to the common end (e15) of means CTC1 and CTC2, where the end (e15) itself is connected to the end (15) of the secondary winding (10) to provide the drive for transistor 40, synchronised by the voltage signal at point e15, denoted V(e15), use to effect the charge transfer from the source (VAUX), available as v60 at the terminals of member 60, to the gate of power switch 30 during the freewheel phase, during which signal V(e15) is more or less zero. This charge is unidirectional, and remains stored on the gate during the freewheel phase. Means CTC1 are therefore means by which said freewheel switch (30) is rendered independent of the voltage at the terminals of the secondary winding (10) during the freewheel phase.

The emitter of the bipolar transistor (40) is connected to the DC voltage source VAUX, obtained here by rectification of the voltage at the end (15) of the secondary winding (10) using the rectifier member (62) and the optional resistance (63). By choosing voltage VAUX as described, a voltage is obtained at the gate of the freewheel MOSFET transistor (30) which varies in the same direction as, and is equivalent to, that available at the gate of the direct MOSFET transistor (20), and therefore proportional to the input voltage. Voltage VAUX can, however, be chosen to be fixed in relation to the voltage of the secondary winding (10) during the direct phase and therefore in relation to the input voltage or varying with the input voltage in proportions which are acceptable for the controlled gate.

In the direct phase, voltage v(e15) becomes positive. Diode 41, mounted in anti-parallel at the base of transistor 40, between points b40 and v60, passes a reverse current in the by-pass RC network (42–43) so as to allow synchronisation and transfer of charge from the source (VAUX) to the gate of the power transistor (30) during the freewheel phase.

Circuit CTC2 includes a bipolar signal transistor (50), known as the anticipation transistor, of the npn type, which enabling anticipation of the cut-off of the freewheel transistor (30) on the change of slope of the voltage at the terminals of the secondary winding (10) In fact, the change of slope is detected by the RC by-pass network composed of capacitor 52 and resistance 53, these two elements being mounted in series and then wired between the base (b50) of transistor 50 and the input (15), where input 15 is itself connected to the end (15) of the secondary winding (10).

The emitter of the anticipation transistor (50) is connected to the drain of the power transistor (20) effecting the direct transfer of energy in the direct phase, the drain of the power transistor itself (20) itself being connected to input 13 of the rectifier (1), and input 13 itself being wired to the output (12) of the secondary winding (10). The collector of the anticipation transistor (50) is connected to the gate (g30) of the freewheel transistor (30) through an impedance (31) which is equated to a short circuit, and the collector is also connected to that of transistor 40 of the means CTC1 circuit forming junction s33.

During the freewheel phase, the voltage at the terminals of the secondary winding (10) is reversed, and voltage V(e15) becomes more or less zero, diode 51 mounted in anti-parallel at the base-emitter junction of the anticipation transistor (50), between points 13 and b50, enables a reverse current in the RC by-pass network 52–53 in order to allow synchronisation and anticipation of removal of the charge from the gate of the power transistor 30 just before the active direct energy transfer phase. The means CTC2 are therefore means for anticipating cut-off of freewheel switch 30 before direct energy transfer switch 20 is switched into conduction in the direct phase.

In this first implementation, the gate of power transistor 20, enabling the direct transfer of energy, is controlled by the secondary power winding (10), and includes known control and protection means (21–22) in self-regulated synchronous rectification.

FIG. 3 shows voltage diagrams for V(e15), V(g20) and V(g30) as a function of time, associated with a converter having a secondary part such as that shown on FIG. 2.

V(e15) is the voltage signal at points 15 of rectifier 1, combined with point e15 at the common end of means CTC1 and CTC2 as a function of time and referenced to the potential of the common sources of the power transistor (20 and 30), connected to ground (0) of the secondary.

V(g20) and v(g30) are the gate voltages of transistors 20 and 30 referenced to the common sources (0) or the ground of the secondary.

During the positive slope phase of the secondary power winding voltage (10), preceding the positive flat portion of signal V(e15), the RC by-pass network (52–53) generates a direct current in the base of the signal transistor (50), which conducts to cancel the gate charge of the MOSFET power transistor (30). The channel of the MOSFET transistor (30) is cut off, and the freewheel current then flows in the parasitic diode of the MOSFET transistor (30) or in an external diode mounted in parallel. The winding voltage continues to increase and generates a positive charge on the gate of the direct MOSFET transistor (20) and the resistance of the MOSFET transistor (20) becomes more or less zero in the positive flat portion of signal V(e15). Signal V(e15) is then equal to the voltage at the terminals of the secondary power winding (10)

In the positive flat portion of signal V(e15), charge transistor 40 is cut off. Diode 41 is used to generate a so-called negative current in the RC by-pass network (42–43) in order to allow synchronisation of charge transfer from the auxiliary supply (VAUX) available at V60, to the gate of the MOSFET transistor (30) in the following phase, called freewheel phase. This current in diode 41 and the current available in the feed diode (62) charges the capacitor (60) of the auxiliary supply (VAUX) to a voltage close to the winding voltage available at g20 on the gate of the direct MOSFET transistor (20).

The direct phase ends with a change of slope initiated by the primary control circuit. The resulting negative slope at the terminals of winding 10 and at V(e15) results in an inverse current through diode 51 into the RC by-pass network (52–53) compensating for the positive current induced in the preceding positive slope phase. The anticipation transistor (50) is cut off, thus enabling transfer of charge from VAUX to the gate of the power transistor (30) through charge transistor 40 as soon as the voltage available at V(e15) enables direct polarisation of its base, by virtue of the RC by-pass network (42–43) through which flows the base current of transistor 40, in opposition to the current in diode 41 during the preceding phase. The gate charge available at g30 is thus more or less equal to that which was available at g20. This will be maintained during all of the flat portion where the V(e15) signal is more or less zero, that is the freewheel phase.

The freewheel phase finishes with a change of slope of the voltage at the terminals of the power winding (10) initiated by the primary control circuit. The resulting positive slope anticipates cut-off of the power transistor (30), generating a direct current in the base of the anticipation transistor (50) in the RC network (52–53) as described at the start of the cycle.

Thus, the two MOSFET transistors (20 and 30) are controlled by a more or less identical voltage, and vary in the same direction as the input voltage, the image of which in the secondary stage is the V(e15) signal available at winding 10 during the direct phase.

FIG. 4 schematically shows the secondary part (100) of a direct energy transfer converter according to a second embodiment of the invention.

This secondary part (100) is identical to that represented on FIG. 2, except that it includes two other charge-transfer circuits (CTC1$d$ and CTC2$d$), in order to generate the drive for the direct transistor (20), which depends only on the voltage source (VAUX).

The circuit CTC1$d$ is created in an identical manner to circuit CTC1, and includes:
a bipolar transistor (40$d$),
a resistance (42$d$),
a capacitance (42$d$),
a diode (41$d$).

The circuit CTC2$d$ includes:
a MOSFET transistor (50$d$) called delay transistor,
a capacitance (52$d$),
a resistance (53$d$),
a diode (51$d$).

The circuit CTC1 operates in an identical manner to circuit CTC1, and provides the charge for the gate of direct transistor 20.

The resistance 53$d$ has one end connected to the gate of the freewheel transistor (30) via resistance 31, and the other end connected to the gate of the delay transistor (50$d$).

The capacitance (52$d$) has one end connected to the gate of the delay transistor (50$d$) and the other end connected to the source of the direct transistor (20).

Regarding circuit CTC2$d$, diode 51$d$ provides for the discharge of the direct transistor (20). MOSFET transistor 50$d$, capacitance 52$d$, and resistance 53$d$ delay the rise of the charge at the gate of transistor 20 while a charge is present at the gate of transistor 30.

FIG. 5 schematically shows the secondary part (10) of a direct energy-transfer converter, according to a third embodiment of the invention.

The secondary part (100) here includes two power windings (10 and 10$b$) wired in phase opposition on rectifier transistors 20 and 30, and thus perform "full-wave" asymmetrical synchronous rectification with active clamping. Circuits CTC1, CTC2, CTC1$d$ and CTC2$d$ are created in an identical manner to the circuit shown on FIG. 4, but the synchronisation signals of these circuits change, since the signal available at point 15, the common point of then two windings (10 and 10$b$), is more or less continuous.

Thus the synchronisation signal for circuits CTC1 and CTC2 is taken from point 13$b$ connecting the drain of transistor 30 to the end (14$b$) of winding 10$b$.

Likewise, the member 51$d$, assisting with cut-off of transistor 20, is connected to point 13$b$.

As for FIGS. 2 and 4, the charge-transfer circuits, CTC1, CTC2 and CTC1$d$, are synchronised by variable transformer winding signals. Circuits CTC1 and CTC1$d$ provide a drive for the gate of each of the transistors (20 and 30) which is proportional to the input voltage. Note again that this drive voltage can also be independent of the input voltage if an independent voltage (VAUX) is used.

Of course, the invention is not limited to the embodiments described above.

In particular, the so-called anticipation and charge transistors have been described as bipolar transistors, but these can equally well be MOSFET signal transistors.

The invention claimed is:

1. A direct energy-transfer converter, which includes:
   a primary stage with at least one transformer primary winding and one controlled switch presenting conducting and non-conducting operating phases,
   a secondary stage including at least one secondary winding (10) of said transformer, and a synchronous rectifier (1), including:
      at least a first switch (20), known as the direct switch, which is self-regulated and conducting during the conducting phases of said controlled switch of the primary stage, known as the direct energy-transfer converter phases,
      at least a second switch (30), known as the freewheel switch, which is self-regulated and conducting during the non-conducting phases of said controlled switch of the primary stage, known as the freewheel phases, an output filter (5),
   where said converter possesses the first self-regulated means which are triggered as a function of the voltage at the terminals of said secondary winding (10), and applying to said second switch (30) a corresponding control voltage suitable to make the second switch (30) conduct,
   wherein said first self-regulated means include a first charge-transfer circuit (CTC1) which is directly controlled by said voltage at the terminals of said secondary winding (10) to apply to said second switch (30) a control voltage which is more or less constant and supplied by an auxiliary voltage source (VAUX), and said first and second switches (20 and 30) are MOSFET transistors, and said charge-transfer circuit (CTC1) includes:
      a by-pass network which includes a capacitor (42) connected in series with a resistance (43), where said resistance is connected to one end (14) of said secondary winding (10), said circuit detecting the variation in the voltage induced by said primary winding at the terminals of said secondary winding (10), and
      a bipolar transistor (40), known as the charge transistor, where the base of said bipolar transistor us controlled via said circuit, where the emitter of said bipolar transistor is connected to said auxiliary voltage source and where the collector of said bipolar transistor is connected to the gate of the second switch (30).

2. A converter according to claim 1, wherein said auxiliary voltage source (VAUX) supplies a voltage (V60) which is more or less equal to the voltage of the secondary winding (V10) during the direct phase.

3. A converter according to claim 1, wherein the control voltage of said first switch (20) is obtained from the voltage at the terminals of said secondary winding (10).

4. A converter according to claim 1, wherein said converter, which includes second self-regulated means to apply a control voltage which will render conducting said first switch (20) in the direct phase, where this control voltage is supplied by said auxiliary voltage source (VAUX) by means of a second charge-transfer circuit (CTC1d).

5. A converter according to claim 1, wherein a diode (41) is mounted in anti-parallel between the base and emitter of said bipolar charge transistor (40).

6. A converter according to claim 1, wherein it includes the means (CTC2) to anticipate the cut-off of said second switch (30) before switching into conduction of the first switch (20) in said direct phase.

7. A converter according to claim 6, wherein said first and second switches (20 and 30) are MOSFET transistors, and said means (CTC2) to anticipate the cut-off of said second switch (30) before the switching into conduction of said first switch (20) in said direct phase includes:
   a by-pass network which includes A capacitance (52) connected in series with a resistance (53), where said resistance is connected to one end (14) of said secondary winding (10), said circuit detecting the variation in the voltage induced by said primary winding at the terminals of said secondary winding (10), and
   a bipolar transistor (50), known as the anticipation transistor, where the base of said bipolar transistor is controlled via said by-pass network, where the emitter of said bipolar transistor is connected to the drain of said first switch and the collector of the bipolar transistor is connected to the gate of said second switch.

8. A converter according to claim 7, wherein a diode (51) is connected in anti-parallel between the base and emitter of said anticipation bipolar transistor.

9. A converter according to claim 4, wherein said first and second switches (20 and 30) are MOSFET transistors, and said second charge-transfer circuit (CTC1d) includes:
   a by-pass network which includes a capacitor (42d) connected in series with a resistance (43d), said resistance being connected to one end of said secondary winding (10), said circuit detecting the variation in the voltage induced by said primary winding at the terminals of said secondary winding (10), and
   a bipolar transistor (40), known as the charge transistor, where the base of said bipolar transistor is controlled via said circuit, where the emitter of said bipolar transistor is connected to said auxiliary voltage source (VAUX) and where the collector of said bipolar transistor is connected to the gate of the first switch (20).

10. A converter according to claim 1, wherein it includes the means (CTC2d) to delay the switching into conduction of said first switch (20) while said second switch (30) is controlled.

11. A converter according to claim 10, wherein said first and second switches (20 and 30) are MOSFET transistors, and in that said means (CTC2d) to delay the switching into conduction of the first switch (20) while the second switch (30) is controlled, includes:
   a MOSFET transistor (50d), called the delay transistor,
   a resistance (53d) with one end connected to the gate of said freewheel transistor (30) and the other end connected to the gate of said delay transistor (50d), and
   a capacitance (52d) with one end connected to the gate of said delay transistor (50d) and a second end connected to the source of said direct transistor (20).

12. A converter according to claim 1, wherein the secondary stage includes two secondary windings (10, 10b) wired in phase opposition on first and second switches (20, 30) so as to perform full wave asymmetrical synchronous rectification.

* * * * *